United States Patent [19]

Mushabac

[11] Patent Number: 5,257,184
[45] Date of Patent: Oct. 26, 1993

[54] METHOD AND APPARATUS WITH MULTIPLE DATA INPUT STYLII FOR COLLECTING CURVILINEAR CONTOUR DATA

[76] Inventor: David R. Mushabac, 919 Ocean Ave., Brooklyn, N.Y. 11226

[21] Appl. No.: 694,101

[22] Filed: May 1, 1991

Related U.S. Application Data

[63] Continuation-in-part of Ser. No. 507,162, Apr. 10, 1990.

[51] Int. Cl.[5] .................. G06F 15/42; A61C 19/04
[52] U.S. Cl. .................. 364/413.28; 433/72; 356/68; 356/72
[58] Field of Search .............. 364/474.03, 474.05, 364/474.29, 474.36, 413.28; 433/72, 229; 356/2, 25–26, 34, 68, 72, 229; 128/776–777; 382/60

[56] References Cited

U.S. PATENT DOCUMENTS

| | | |
|---|---|---|
| 3,971,133 | 7/1976 | Mushabac . |
| 4,182,312 | 1/1980 | Mushabac . |
| 4,239,431 | 12/1980 | Davini . |
| 4,349,277 | 9/1982 | Mundy et al. . |
| 4,431,420 | 2/1984 | Adair . |
| 4,436,684 | 3/1984 | White .................. 264/138 |
| 4,525,858 | 6/1985 | Cline et al. . |
| 4,564,295 | 1/1986 | Halioua . |
| 4,575,805 | 3/1986 | Moermann et al. .......... 433/68 |
| 4,577,968 | 3/1986 | Makosch . |
| 4,611,288 | 9/1986 | Duret et al. .............. 364/474.05 |
| 4,657,394 | 4/1987 | Halioua . |
| 4,663,720 | 5/1987 | Duret et al. .............. 364/474.05 |
| 4,734,034 | 3/1988 | Maness et al. .............. 433/68 |
| 4,763,791 | 8/1988 | Halverson et al. .......... 206/570 |
| 4,837,732 | 6/1989 | Brandestini et al. ........ 395/150 |
| 4,936,862 | 6/1990 | Walker et al. ............... 623/23 |
| 4,941,826 | 7/1990 | Loran et al. ................ 433/451 |
| 4,997,369 | 3/1991 | Shafir ....................... 433/72 |
| 5,016,199 | 5/1991 | McMurty et al. .......... 364/474.03 |
| 5,121,333 | 6/1992 | Riley et al. ................ 364/474.05 |

OTHER PUBLICATIONS

Boone, P. M., Optical Methods to Measure Shape and Size, Oct. 1987.
Boone, P. M. Optical Methods to Measure Shape and Size, University of Gent.

Primary Examiner—Gail O. Hayes
Attorney, Agent, or Firm—R. Neil Sudol; Henry D. Coleman

[57] ABSTRACT

A device for providing a computer with electrically encoded data specifying curvilinear contours of an object comprises a manipulable frame member, componentry for establishing a reference position, a plurality of stylus elements, and means for measuring displacements of the stylii along respective axes. The componentry for establishing a reference position includes circuits for transmitting to the computer an electrical signal encoding a location of a reference point on the frame member. The stylus elements are each slidably mounted to the frame member for motion along respective axes extending at least partially parallel to one another. The means for measuring or detecting stylus displacements is operatively connected to the stylus elements for transmitting to the computer electrical signals encoding displacements of the stylii along the respective axes.

19 Claims, 10 Drawing Sheets

METHOD AND APPARATUS WITH MULTIPLE DATA INPUT STYLII FOR COLLECTING CURVILINEAR CONTOUR DATA

CROSS-REFERENCE TO A RELATED APPLICATION

This application is a continuation-in-part of commonly owned Application Ser. No. 507,162 filed Apr. 20, 1990.

FIELD OF THE INVENTION

This invention relates to a method and apparatus for gathering contour data. More specifically, this invention relates to a method and apparatus for generating signals encoding contours of a surface of a three-dimensional object. The signals are fed to a computer and may be used in graphically displaying an image of the object on a computer monitor and for modifying the shape of the object via a CAD/CAM type process.

BACKGROUND OF THE INVENTION

U.S. Patent Application Ser. No. 507,162 discloses a system for modifying the shape of a three dimensional object such as a tooth in a patient's mouth. The system includes a pantograph type assembly for feeding to a computer digitized data representing surface contours of the tooth. The pantograph assembly includes a handheld probe inserted into the patient's mouth by a dentist. The dentist manipulates the probe so that a stylus tip of the instrument is held in contact with the tooth during tracing of a contour along the tooth. A pantograph extension outside the patient's mouth tracks the motion of the probe and particularly the stylus tip thereof, the motion of the pantograph extension being monitored by cameras which transmits video signals to the computer.

An improvement in the gathering of the contour data is disclosed in commonly owned U.S. Patent Applicatoin Ser. No. 613,354, still pending, filed Nov. 14, 1990 as a continuation-in-part of Ser. No. 507,162 still pending. In accordance with that disclosure, tape strips are adhesively applied to tooth surfaces The tape strips are formed with parallel guides such as slots or beads for guiding the stylus tip of the dental probe along a plurality of parallel lines The gathering of surface data along parallel lines greatly facilitates the processing of the data by off-the-shelf CAD/CAM programs.

OBJECTS OF THE INVENTION

An object of the present invention is to provide another method and apparatus which facilitates the collection of surface data, particularly from a surface of a tooth.

Another object of the present invention is to provide such a method and apparatus for gathering surface data which is easily processed by conventional CAD/CAM type programs.

Another, more particular, object of the present invention is to provide such a method and apparatus for gathering surface data along a plurality of parallel contour lines.

SUMMARY OF THE INVENTION

A device for providing a computer with electrically encoded data specifying curvilinear contours of an object comprises, in accordance with the present invention, a manipulable frame member, componentry for establishing a reference position, a plurality of stylus elements, and means for measuring displacements of the stylii along respective axes. The componentry for establishing a reference position includes circuits for transmitting to the computer an electrical signal encoding a location of a reference point on the frame member. The stylus elements are each slidably mounted to the frame member for motion along respective axes extending at least partially parallel to one another. The means for measuring or detecting stylus displacements is operatively connected to the stylus elements for transmitting to the computer electrical signals encoding displacements of the stylii along the respective axes.

Pursuant to another feature of the present invention, componentry for establishing the reference position includes a pantograph extension rigid with the frame member and a scanner for optically scanning the location of a point on the pantograph extension and transmitting a resulting video signal to the computer.

In accordance with a specific embodiment of the present invention, the contour data gathering device further comprises a data reference for enabling the computer to determine, via video signals from the scanning means, the location of the point on the pantograph extension relative to the object. Preferably, exactly one of the reference and the scanner is fixed relative to the object or tooth being scanned. The reference may take the form of a grid attached to the object and the scanner may include at least two cameras, for example, in the form of solid state optical sensors attached to the object.

Pursuant to a further feature of the present invention, the stylus displacement measuring means includes a scanner or camera for optically scanning points on the stylus elements. To facilitate detection of the stylii during the scanning operating, the stylus elements are provided with light emitting elements.

As an alternative to optical scanning, the stylii are operatively connected to voltage divider circuits for sensing the displacment of the stylii relative to home positions. Advantageously, the stylus elements are spring biased into the extended home positions relative to the frame member.

The stylus elements may be disposed in a linear array. Alternatively, the stylus elements may be disposed in a two-dimensional array.

Pursuant to another feature of the present invention, the contour data gathering device includes means for transmitting a signal to the computer that data input from the stylus displacement measuring means is taking place.

A method for providing a computer with digitized data encoding surface features of a three-dimensional object comprises, in accordance with the present invention, the steps of (a) providing a manipulable frame member having a plurality of stylus elements each slidably mounted to the frame member for motion along respective axes extending at least partially parallel to one another, (b) tracing at least one surface contour on the three-dimensional object with the manipulable frame member so that the stylus elements are in contact with the object, (c) transmitting to the computer an electrical signal encoding a location of a reference point on the frame member during the step of tracing, and (d) transmitting to the computer electrical signals encoding displacements of the stylii along the respective axes during the step of tracing.

Pursuant to another feature of the present invention, the manipulable frame member is provided with a pantograph extension rigid therewith. The step of transmitting to the computer an electrical signal encoding a location of a reference point the includes the step of optically scanning the location of a point on the pantograph extension and transmitting a resulting video signal to the computer.

Pursuant to an additional feature of the present invention, the step of transmitting to the computer electrical signals encoding displacements of the stylii includes the step of optically scanning points on the stylus elements. Alternatively, the step of transmitting to the computer electrical signals encoding displacements of the stylii includes the step of generating electrical signals using a plurality of voltage dividers.

In another step, the computer is signaled that data input from the stylus displacement measuring means is taking place.

In an apparatus or the associated method in accordance with the present invention, the collection of contour data from the surface of an object in a plurality of parallel planes is greatly facilitated. The data collection process is quick and easy and utilizes hand motions to which dentists are accustomed.

DETAILED DESCRIPTION OF THE INVENTION

Figure 1:
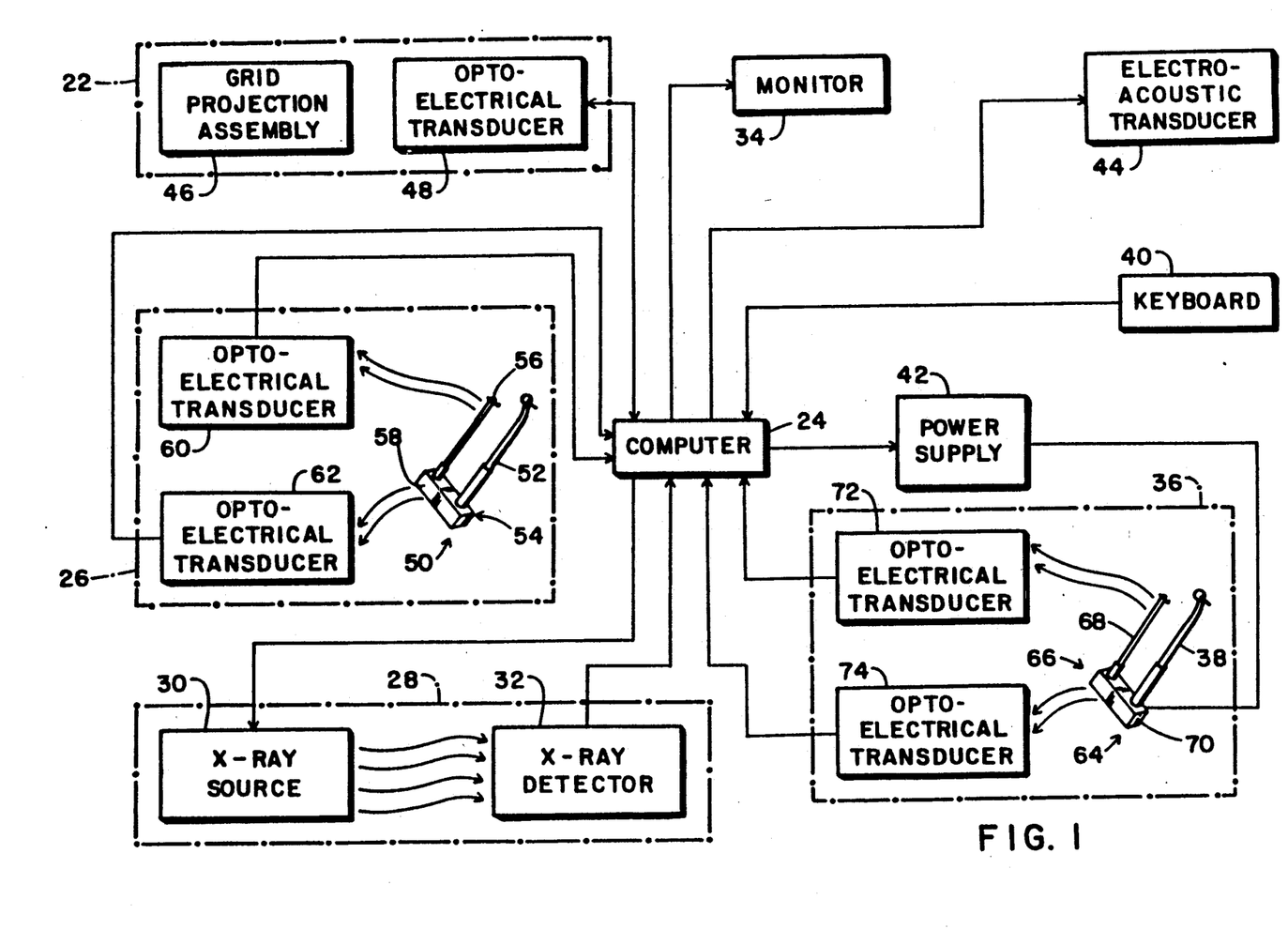
FIG. 1 is a block diagram of a system effecting a desired modification in the shape of a pre-existing object such as a tooth to which access is restricted.

As illustrated in FIG. 1, a computerized interactive system for producing a modification in the shape of an object such as a tooth to which access is limited comprises a first data generating device or assembly 22 for providing a computer 24 with electrically encoded data, specifically, digitized video signals representing a three-dimensional surface of an object such as a tooth. A second data generating device or assembly 26 is operatively connected to computer 24 for transmitting thereto digitized video signals containing information pertaining to a curvilinear contour on the surface of the three-dimensional surface of the tooth. In addition, computer 24 may receive from a third data generating device or assembly 28 digitized input signals relating to internal structures of the tooth being scanned. Specifically, data generating device 28 may take the form of an X-ray device such as used in current intra-oral radiology or other methodologies and basically comprises a source 30 of X-ray radiation and a detector 32 for receiving the X-ray radiation after it passes through a tooth and converting the incident radiation into a digital data stream fed to computer 24.

As further illustrated in FIG. 1, the computerized interactive dentistry system also comprises a display device 34 such as a monitor or holographic projector. In response to data signals, computer 24 generates a three-dimensional view on display of monitor 34 of the tooth or teeth under examination. More specifically, computer 24 is provided with any commercially available stereophotogrammetric triangulation program for calculating and displaying, on the basis of the video input signals from data generating devices 22, 26 and 28, three dimensional surfaces and contours of the tooth or teeth.

The computerized interactive dentistry system of FIG. 1 further includes another data generating device or assembly 36 which provides computer 24 with digitized video information as to the location of the operative tip of a cutting instrument 38 such as a dentist's drill relative to the three-dimensional structural features of the tooth. Data generating device 36 thus enables computer 24 to monitor modifications to the shape of the tooth as those modification are being made in the tooth.

The system of FIG. 1 is further provided with any of several instruction input devices such as a keyboard 40, a mouse (not shown), or a contact sensitive surface of monitor 34, whereby an operator such as a dentist or dental technician may instruct the computer to display on monitor 34 a graphic representation of a tooth preparation which has been previously defined or input into the computer as a digitized "blueprint." The blueprint is generally a generic form but may be adapted to the individual as described hereinafter. In addition, or alternatively, computer 24 may use input from drill data generating device 36 as instructions regarding, for example, the depth of a tooth preparation to be displayed on monitor 34.

Upon selecting a desired tooth preparation illustrated on monitor 34, the dentist operates drill 38 to cut a recess into the tooth (in the case of a filling or inlay) or or to remove an outer layer of the tooth (in the case of preparing a form/shape for a crown or other prosthetic resotration). Computer 24 monitors the location of the operating tip of the drill via data generating device 36 and, if the drill approaches a boundary previously defined to the computer during an interactive tooth preparation selection operation, either interrupts the power provided to the drill via a supply 42 or alerts the dentist via a signaling device such as an electro-acoustic transducer 44.

As depicted schematically in FIG. 1 and discussed in greater detail hereinafter, data generating device 22 includes a grid projection assembly 46 for optically imposing a grid onto the surface of the patient's tooth. Data generating device 22 also includes an opto-electrical transducer 48 such as a charge-coupled device for optically sensing or scanning the tooth surface onto which the grid is projected by assembly 46. It is to be understood that the grid pattern projected on the tooth surface need not be an orthogonal grid having two sets of lines at right angles to one another, but may instead have the two sets of lines oriented at an acute angle. Moreover, although the preferred embodiments of the present invention incorporate an optical grid, it is to be appreciated that the invention also contemplates that a grid may be imposed onto the tooth surface by other methods, such as adhesively attaching to the tooth surface a transparency provided with a grid.

As further depicted in FIG. 1 and described in detail hereinafter, data generating device 26 comprises a pantographtype component 50 which incorporates a stylus member 52 and a pantograph extension 54 in turn including a pantograph arm 56 and a bridge element 58. Bridge element 58 connects pantograph arm 56 to stylus member 52. Data generating device 26 further comprises at least a pair of opto-electrical transducers 60 and 62 preferably in the form of respective charge-coupled devices ("CCD"s). Pantograph component 50 enables computer 24 to track, from outside the mouth, the motions of the tip of the stylus member inside the mouth and even beneath the gum line.

Accordingly, data generating devices 22, 26 and 28 provide to computer 22 electrically encoded data completely defining the structure of the tooth on which a dentist is working. Computer 24 then "draws" the tooth on monitor 34. At that juncture the dentist instructs the computer to modify the displayed threedimensional shape. For example, the dentist may use keyboard 40 to input a command that a predefined tooth preparation from an electronic memory or other storage resource be overlaid in graphic form on the three-dimensional graphic representation of the tooth. The size of the tooth preparation relative to the tooth may be specified by entering depth, width or length dimensions or contour areas via keyboard 40, data generating device 36, a mouse or a contact-sensitive surface of monitor 34. Alternatively, computer 24 may be programmed to automatically select a possible tooth preparation based on analytic programs of tooth forms or prior stored forms, in accordance with the data from data generating devices 22, 26 and 28. In accordance with yet another alternative procedure, the dentist may command the computer to alter the graphic representation of the tooth, for example, by removing a layer of several millimeters from a surface selected by the dentist or by removing a selected volume of tooth from all five surfaces above the gum line to a contour below the gum line defined by the second data generating device 26.

As further depicted in FIG. 1 and described in detail hereinafter, data generating device 36 comprises a pantographtype component 64 which incorporates drill 38 and a pantograph extension 66 in turn including a pantograph arm 68 and a bridge element 70. Bridge element 70 connects pantograph arm 68 to drill 38. Data generating device 36 further comprises at least a pair of opto-electrical transducers 72 and 74 preferably in the form of respective charge-coupled devices ("CCD"s). Pantograph component 64 enables computer 24 to track, from outside the mouth, the motions of the tip of drill 38 inside the mouth and even inside a tooth.

In a preferred embodiment of the invention, data generating device 36 is the same as data generating device 26 with stylus element 52 replaced by drill 38. Moreover, upon the selection of a desired tooth preparation via computer 24, monitor 34 and an instruction input device such as keyboard 40, drill 38 is used by the dentist to provide the displayed tooth preparation in the subject tooth. Computer 24 monitors the output signals of opto-electrical transducers 72 and 74 thereby tracks the cutting motions of the operating tip of drill 38 inside the subject tooth. The excavations into the tooth are displayed in real time on monitor 34 by computer 24.

Figure 2:
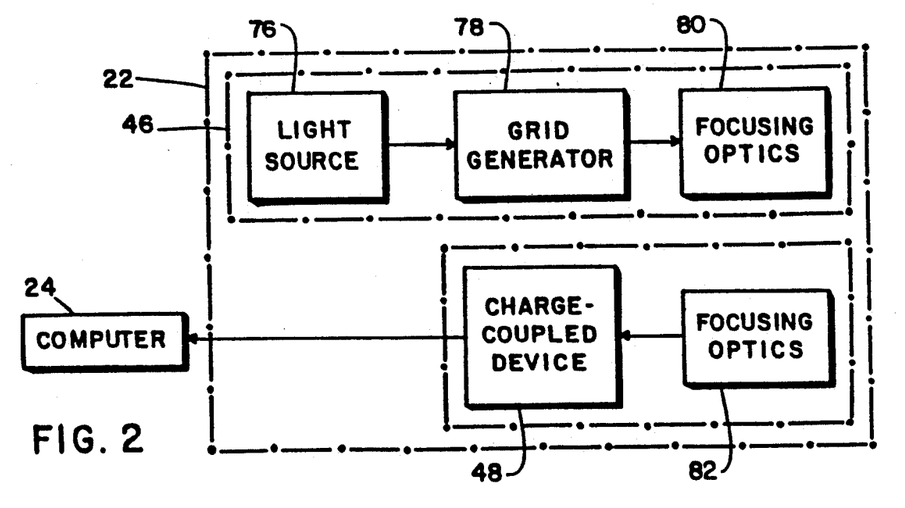
FIG. 2 is a block diagram showing details of a surface data generating device shown in FIG. 1.

As shown in FIG. 2, grid projection assembly 46 of data generating device 22 includes a light source 76, a grid generator 78 and an assembly 80 of light guides and lenses for guiding the grid light along a path through the data generating device and for focusing the grid light on the surface of a subject tooth. The light subsequently reflected from the tooth surface is gathered by further optical elements 82 and focused by those elements on the light sensitive sensor surface of charge-coupled device ("CCD") 48. In response to a sensed pattern of light intensities, CCD 48 generates and transmits to computer 24 a digitized video signal containing information used by computer 24 to calculate the dimensions of the subject tooth and to display the tooth's structure in a three-dimensional graphic representation on monitor 34.

Figures 3, 4:
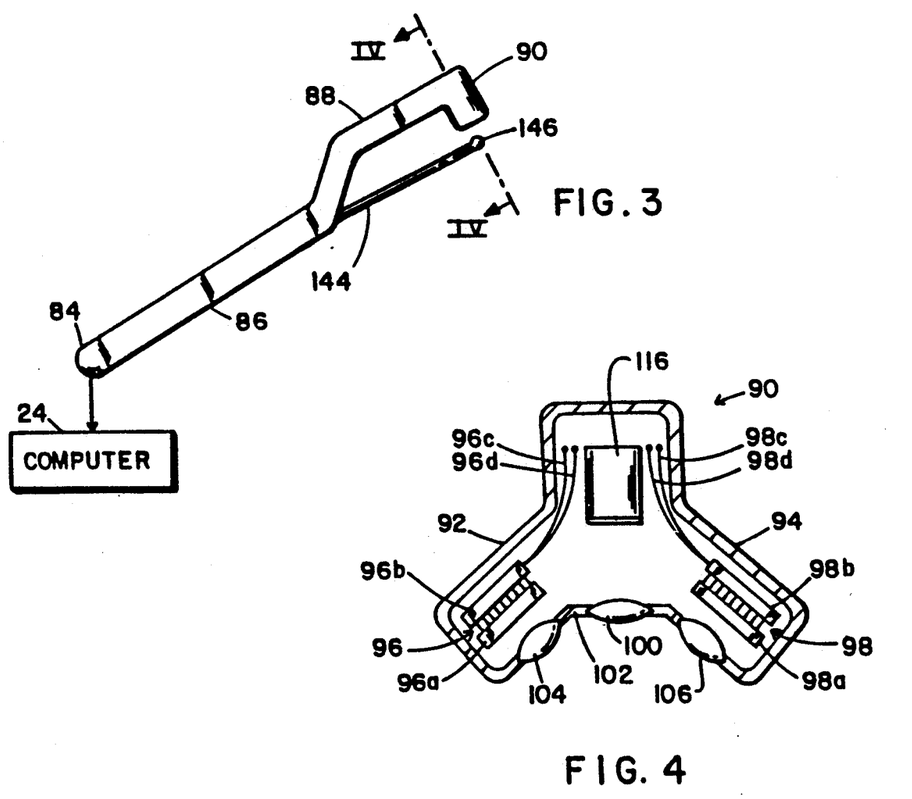
FIG. 3 is partially a block diagram and partially a schematic elevational view of a particular embodiment of the surface data generating device of FIG. 2.
FIG. 4 is a cross-sectional view taken along line IV—IV in FIG. 3.

As shown in FIG. 3, the components 76, 78, 80, 82 and 48 of data generating device 22 may be housed in an elongate instrument frame or holder 84 including a handle 86 and a stem portion 88 displaced laterally with respect to a longitudinal axis of handle 86.

In a preferred form of the grid projection instrument, illustrated in detail in FIG. 4, holder 84 of FIG. 3 further includes a Y-shaped distal end portion 90 having a pair of hollow legs 92 and 94 housing respective CCDs 96 and 98. Each CCD includes a respective photosensitive sensor array 96a and 98b and respective sequencing and processing electronics 96b and 98b.

The sequencing and processing electronics 96b and 98b have input and output leads 96c, 96d and 98c, 98d extending to computer 24 through stem portion 88.

Light containing a grid pattern is projected from Y-shaped distal end portion 90 through a focusing lens 100 mounted in a wall 102 between legs 92 and 94. The light subsequently reflected from a subject tooth is focused on sensor arrays 96a and 98a by a pair of lenses 104 and 106 disposed in legs 92 and 94. Lenses 104 and 106 may be considered parts of focusing optics 82 (FIG. 2), while lens 100 is part of focusing optics assembly 80.

Figure 5:
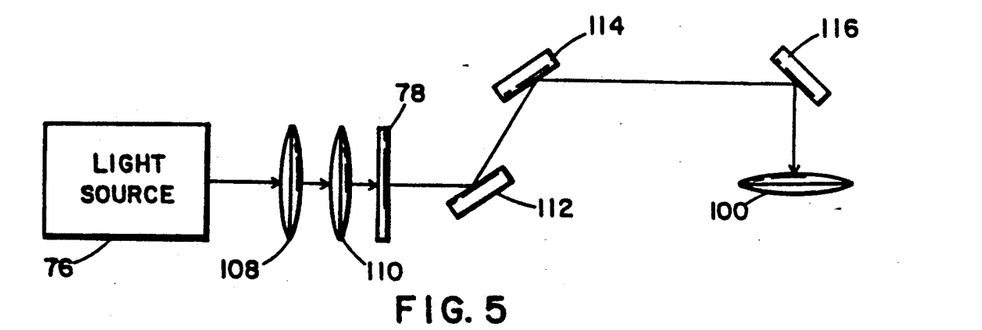
FIG. 5 is a detailed schematic diagram of optical components in a grid projection assembly included in the surface data generating device of FIG. 3.

As shown in detail in FIG. 5, grid projection assembly 46 includes light source 76 (also shown in FIG. 2), a pair of collimating lenses 108 and 110, grid generator 78 (see FIG. 2) in the form of a plate provided with a grid pattern, and three mirrors or prisms 112, 114, 116 for directing the grid-containing light rays through stem portion 88 (FIG. 3) to lens 100. Of course, frame or holder 84 may be provided with various movable mounting elements (not shown) for adjusting the focuses of the various lenses.

Figure 6:
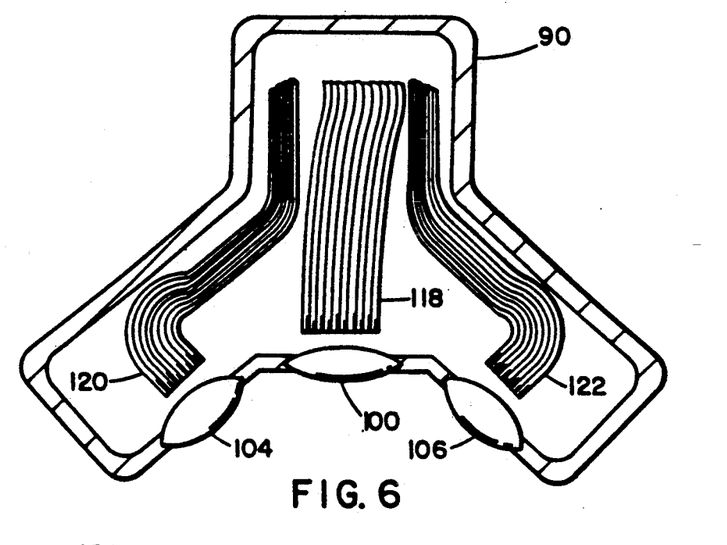
FIG. 6 is a cross-sectional view, similar to FIG. 4, of another particular embodiment of the surface data generating device of FIG. 2.

It is within the contemplation of the invention that the grid light may be guided through the grid projection instrument or frame 84 by elements other than those illustrated in FIG. 5. As depicted in FIG. 6, an output array of light beams is guided to lens 100 by a bundle 118 of optical fibers, while a pair of optical fiber input bundles 120 and 122 receive incoming optical radiation focused on the input ends of bundles by lenses 104 and 108.

Fiber bundles 120 and 122 guide the incoming radiation to a pair of CCDs (not shown) disposed in instrument frame 90 at a more proximal end of the frame, for example, in the handle. Rather than two separate CCDs, the first data generating device 22 may include a single CCD (not shown) disposed in the handle 84 (FIG. 3) and means for directing light from two separate optical pathways to the CCD.

Figure 7:
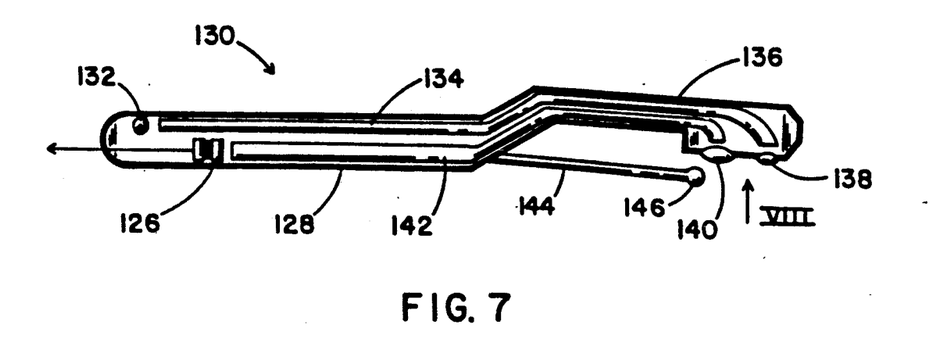
FIG. 7 is a schematic cross-sectional longitudinal view of yet another particular embodiment of the surface data generating device of FIG. 2.
Figure 8:
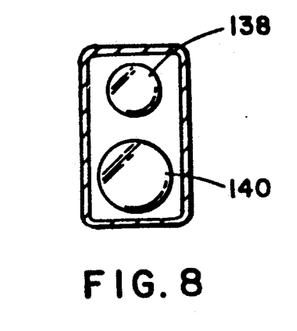
FIG. 8 is an elevational view of a distal end of the embodiment of FIG. 7, taken in the direction of arrow VIII.

As schematically shown in FIGS. 7 and 8, a data generating device or optical probe 124 may incorporate a single CCD transducer 126 disposed in a handle 128 of an elongate instrument frame or casing 130. The handle 128 also houses a grid source 132. An optical fiber bundle 134 guides a grid pattern from grid source 132 through a part of handle 128 and a stem portion 136 of frame 130 to a distal end of the probe. At the distal end, the grid pattern is focused by a lens 138 onto a subject tooth, the reflected radiation pattern being focused by another lens 140 onto the distal or input end of another fiber optic bundle 142 extending to CCD 126.

As shown in FIGS. 3 and 7, frame member 84 and optical probe frame 130 are provided with a stylus element 144 having an enlargement 146 at its distal end. Enlargement 146 is disposable in the visual field of the respective optical scanning element or elements, whether CCD 48, CCDs 96 and 98, or CCD 126, for providing computer 24 with a reference distance or dimension at the surface of a subject tooth being scanned. Computer 24 is thereby able to calculate absolute values for the dimensions of various surface features. Computer 24 measures distances by calculating the number of pixels in the respective sensor array (e.g., 96a and 98a) which cover a feature whose dimensions are being determined. Inasmuch as computer 24 is preloaded with the actual dimensions of enlargement 146, the computer is able to compute actual distances by comparing the number of pixels corresponding to enlargement 146 with the number of pixels corresponding to the features of the tooth.

Stylus element 144 is retractable into handle 86 or 128. Retraction may be implemented either manually or automatically, for example, by a small motor and rack and pinion (not illustrated) inside the respective handle. Moreover, stylus 144 is advantageously replaceable by other elements such as stylus 148 shown in FIG. 9 or stylus 150 shown in FIG. 10.

Figure 9:
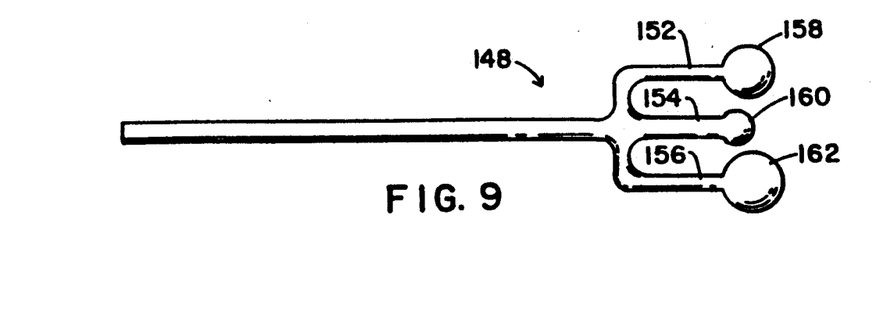
FIG. 9 is a plan view of a reference stylus usable in conjunction with the data generating device of FIGS. 3 and 7.
Figure 10:
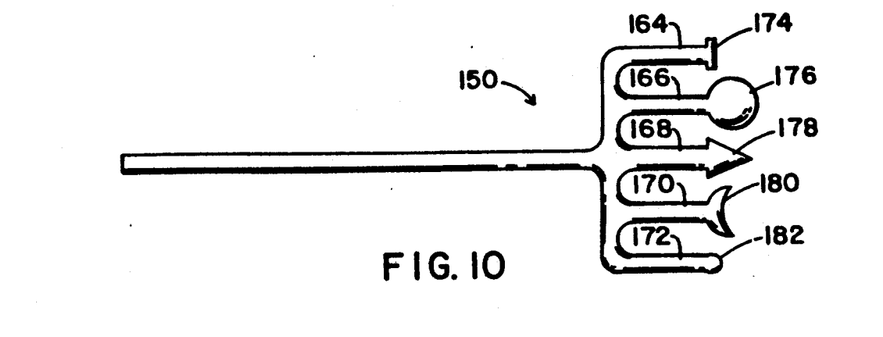
FIG. 10 is a plan view of another reference stylus usable in conjunction with the data generating device of FIGS. 3 and 7.

Stylus 148 is formed at a distal end with three prongs 152, 154 and 156 each having a respective sphere 158, 160 and 162 at its free end. Spheres 158, 160 and 162 may have different sizes for facilitating the measurement of anatomical distances by computer 24. Similarly, stylus 150 has a plurality of prongs 164, 166, 168, 170 and 172 each provided at its free end with an enlarged formation 174, 176, 178, 180 and 182 of a respective geometric shape and a respective transverse dimension.

In using a data generating device equipped with stylus 148, a dentist places at least two of spheres 158, 160 and 162 on the surface of the tooth. Similarly, two enlarged end formations 174, 176, 178, 180 and 182 are positioned in engagement with a tooth surface during use of a data generating device incorporating stylus 150.

Figure 11:
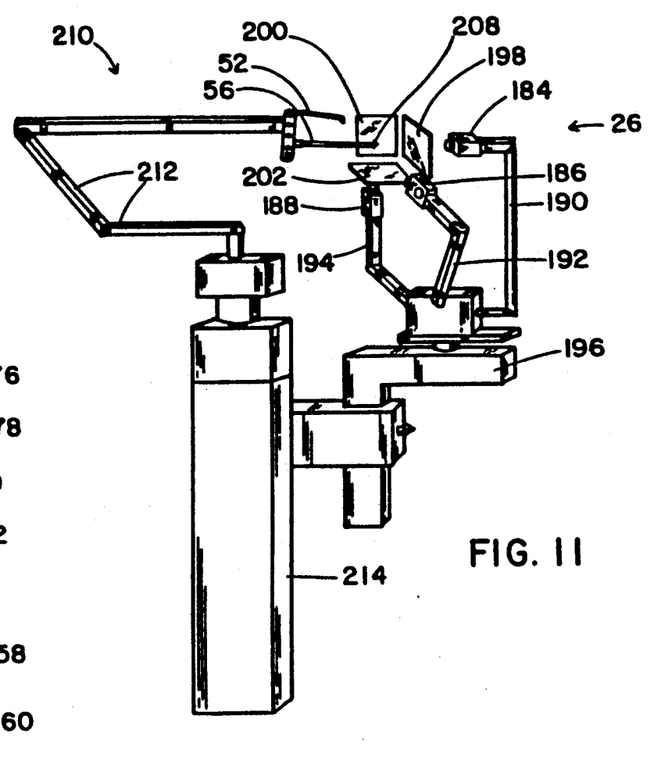
FIG. 11 is a partially diagrammatic perspective view of an embodiment of a contour data generating device shown in FIG. 1.
Figures 12, 13, 14:
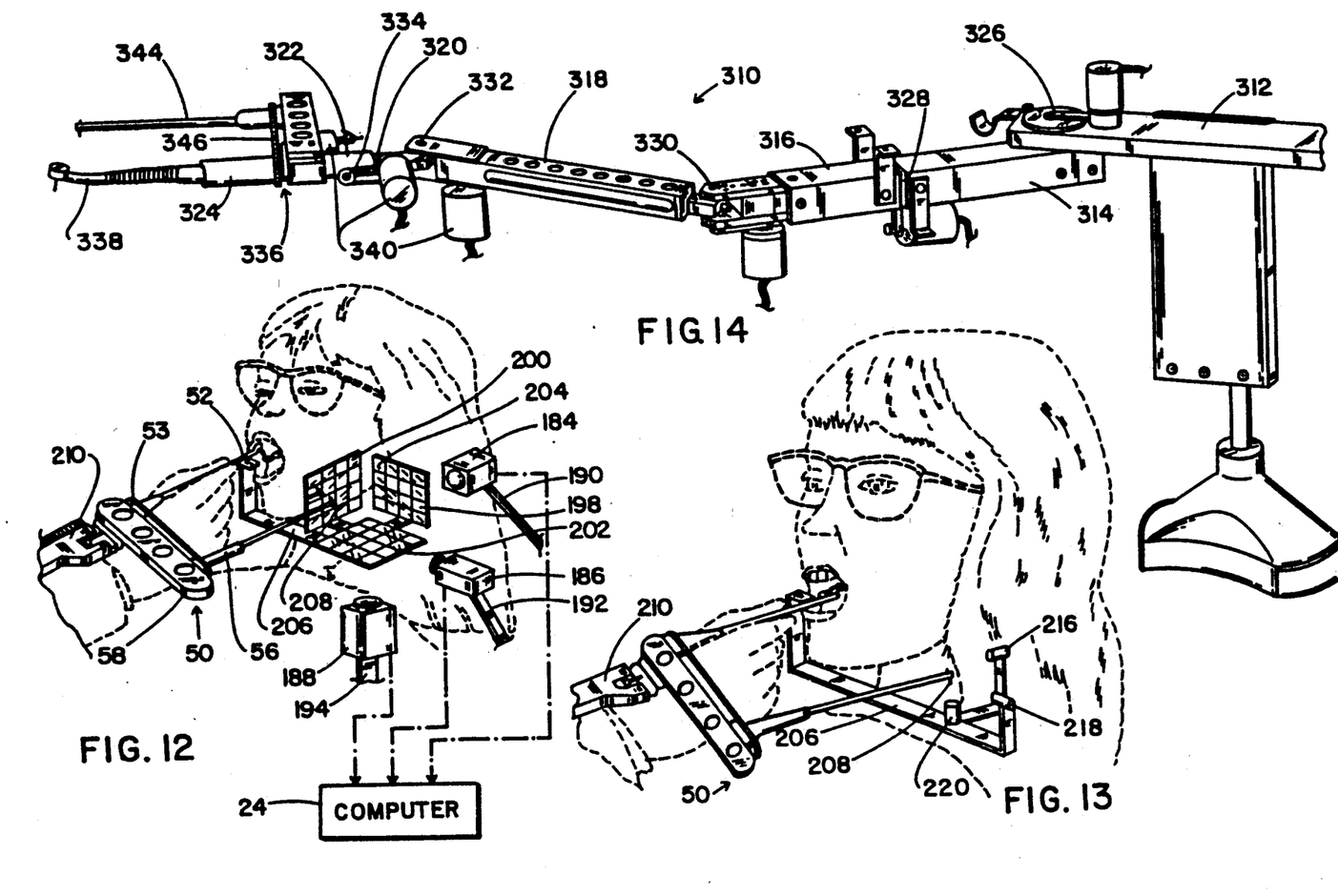
FIG. 12 is a partial perspective view, on an enlarged scale, of the contour generating device of FIG. 11, showing its use with a dental patient.
FIG. 13 is a partial perspective view, on an even larger scale, of another embodiment of the contour generating device of FIG. 1, showing its use with a dental patient.
FIG. 14 is a perspective view of another contour data generating device usable in a dentistry system.

As depicted in FIGS. 11 and 12, contour data generating device 26 (FIG. 1) comprises, in a preferred embodiment of the present invention, three CCD cameras 184, 186 and 188 fixed to the free ends of respective adjustable mounting arms 190, 192 and 194 in turn connected at their other ends to a pedestal member 196. Contour data generating device 26 further comprises three transparent plates 198, 200 and 202 each provided with a respective grid 204 (only one designated in the drawing) and secured to a common substantially L-shaped support arm 206. Support arm 206 is cemented or otherwise attached to the jaw of a patient P prior to the use of the contour data generating device.

It is to be noted that although plates 198, 200 and 202 are illustrated as being orthogonally disposed and as having Cartesian orthogonal grids, it is not necessary for effective calculation of distances and angles that the plates and grids be so oriented. An ordinary modification of the stereophotogrammetric triangulation program is all that is required for the system of FIG. 1 to function with plates 198, 200 and 202 and/or the grid lines thereof oriented at acute angles.

Any two CCD cameras 184, 186 and 188 correspond to opto-electrical transducers 60 and 62 of FIG. 1. Although three CCD cameras are preferred, in some instances two may be sufficient.

As further illustrated in FIGS. 11 and 12, contour data generating device 26 includes pantograph-type component 50. As described hereinabove with reference to FIG. 1 (includes essentially a mirror image of illustrations in FIG. 11 and 12), pantograph component 50 incorporates stylus member 52, pantograph arm 56 and bridge element 58. CCD Cameras 184, 186 and 188 enable computer 24 to track orthogonal components of the motion of a predetermined point 208 on pantograph arm 56 against respective reference frame plates 198, 200 and 200, respectively. Because pantograph arm 56 is fixed with respect to stylus member 52, computer 24 is accordingly able to track, from outside the mouth of patient P, the motions of the tip of the stylus member 52 inside the mouth and even beneath the gum line.

Pantograph component 50 is mounted to the free end of a linkage 210 including a plurality of pivotably interconnected arm members 212. The base of linkage 210, like pedestal member 196 is secured to a base 214.

Both stylus member 52 and pantograph arm 56 are rotatably secured to bridge element 58 so that they can rotate about respective longitudinal axes. Pantograph arm 56 is coupled to stylus member 52 via an endless toothed belt 53 whereby rotation of stylus arm 52 about its longitudinal axis by an operator results in a simultaneous rotary motion of pantograph arm 56.

Accordingly, stylus member 52 is free to be moved by an operator along three translational axes and three rotational axes, the resulting motion being duplicated by pantograph arm 56.

An alternative way for providing computer 24 with a reference frame against which to measure motions of pantograph arm 56 and concomitantly stylus member 52 is illustrated in FIG. 13. In the specific embodiment shown in FIG. 13, three CCD cameras 216, 218 and 220 are fastened to support member 206 in turn cementable, as discussed above, to the patient's jaw in which the subject tooth is rooted. Pursuant to this embodiment of the invention, no reference grids are necessary for computer 24 to monitor, via cameras 216, 218 and 220, the motion of pantograph arm 56 and thus stylus member 52.

It is to be noted that the camera assembly of FIG. 13 essentially includes three pixel arrays (not visible in the drawing) disposed in separate reference planes of a three dimensional coordinate system, with the casings of the cameras serving in part to hold three lenses (not designated with reference numerals) at pre-established distances with respect to the respective pixel arrays to focus the light from the tip 208 of the pantograph arm on the pixel arrays. The tip 208 of pantograph arm 56 may be provided with an LED or other marker element to facilitate detection by the optical scanning assembly comprising cameras 216, 218 and 220.

As illustrated in FIG. 14, contour data may be generated by an alternative technique employing a multiple segment support arm 310 which extends from a fixed platform 312. Support arm 310 includes segments 314, 316, 318, 320, 322 and 324 of which the first segment 314 is connected to platform 312. Segments 314-324 are pivotably connected to one another via six rotating joints 326, 328, 330, 332, 334 and 336. By incorporating six separate junctions for rotational movement, an operating instrument (e.g., drill) 338 connected to the free end of a last or outermost arm 324 can move with six degrees of freedom, specifically along three translational axes and three rotational axes.

Stationary platform 312 and segment 314 are connected at joint 326 to provide rotation relative to one another about a substantially vertical axis. First segment 314 and second segment 316 are coupled to one another for rotation about an axis which is essentially a horizontal axis and which axis is coextensive with the axes of segments 314 and 316. Joint 28 provides this rotational movement. Similarly, arm segments 316 and 318 are rotatably linked via joint 330.

A probe or pantograph-type extension 344 is mounted to the outermost segment 324 and through a belt 346 rotates in synchronism with operating instrument 338. In this fashion, probe 344 is slaved to operating instrument 338. Accordingly, a three-dimensional configuration or contour traced by the tip of operating instrument 338 will be replicated by a tip of pantograph extension 344.

Each joint 326-336 is formed to have sufficient friction to allow the joint to hold a position once placed therein. However, the friction of each joint is low enough so that movement of the joint can be commenced fairly easily.

A plurality of digital encoders 340 are mounted to arm segments 314-324. Upon a movement of operating instrument 338, encoders 340 transmit to computer 24 respective signals encoding the amount of motion in the various six degrees of freedom. The monitoring device of FIG. 14 need not include pantograph extension 344 since motion tracking is accomplished via the encoder output signals rather than optically.

Upon the transmission to computer 24 of sufficient data from surface data generating device 22 and contour data generating device 26 (FIG. 1), computer displays partial or complete graphic representations on monitor 34 of the subject tooth or teeth. The graphic representations include the visible three-dimensional surfaces of each such tooth, as well as invisible base line data fed to computer 24 by contour data generating device 26. In addition, computer 24 may be provided with electrically encoded data specifying internal structures such as the dentine inside each tooth and prior fillings or other prosthetic devices.

Upon viewing a tooth on monitor 34, a dentist may select a preparation which may be appropriate for the particular condition of the tooth. As described above, this selection may be accomplished via an instruction corresponding to an electrically encoded tooth preparation previously loaded into the memory of computer 24. Alternatively, the selection may be implemented by inputting dimensional parameters via keyboard 40, including distances, angles, planes and percentages. As another alternative, computer 24 may provide a menu selection on monitor 34, selections being made from the menu via the keyboard, a mouse or a touch-sensitive monitor screen. In yet another alternative procedure, computer 24 may be programmed to recognize structural features of the tooth, such as its type, the location and shapes of cavities and prior inlays or onlays and to automatically select a possible preparation in accordance with the recognized features. The computer may be further programmed to vary the size of the preparation to correspond to the particular tooth. The dentist would then view the selected preparation and alter it on screen by any of the above-described instruction input techniques. Upon arriving at a final, desired preparation, the dentist will inform computer via keyboard 40.

As discussed hereinabove, drill 38 (FIG. 1) is then used to remove a portion of the subject tooth. Computer 24 may control the supply of power to the drill so that the drill is operational only within the regions selected for removal during the interactive stage of the dental process. Accordingly, drill 38 will be de-energized until the cutting tip of the drill is in near engagement with a surface to be cut. Then computer 24 enables the transmission of power from supply 42 to drill 38. Upon the subsequent approach of the cutting tip of the drill to a defined boundary, as sensed preferably via data generating device 46 (FIG. 1), i.e., via CCD cameras 184, 186, 188 or 216, 218, 220 monitoring a pantograph component 50, computer 24 automatically interrupts power transmission from supply 42 to drill 38.

Figure 15:
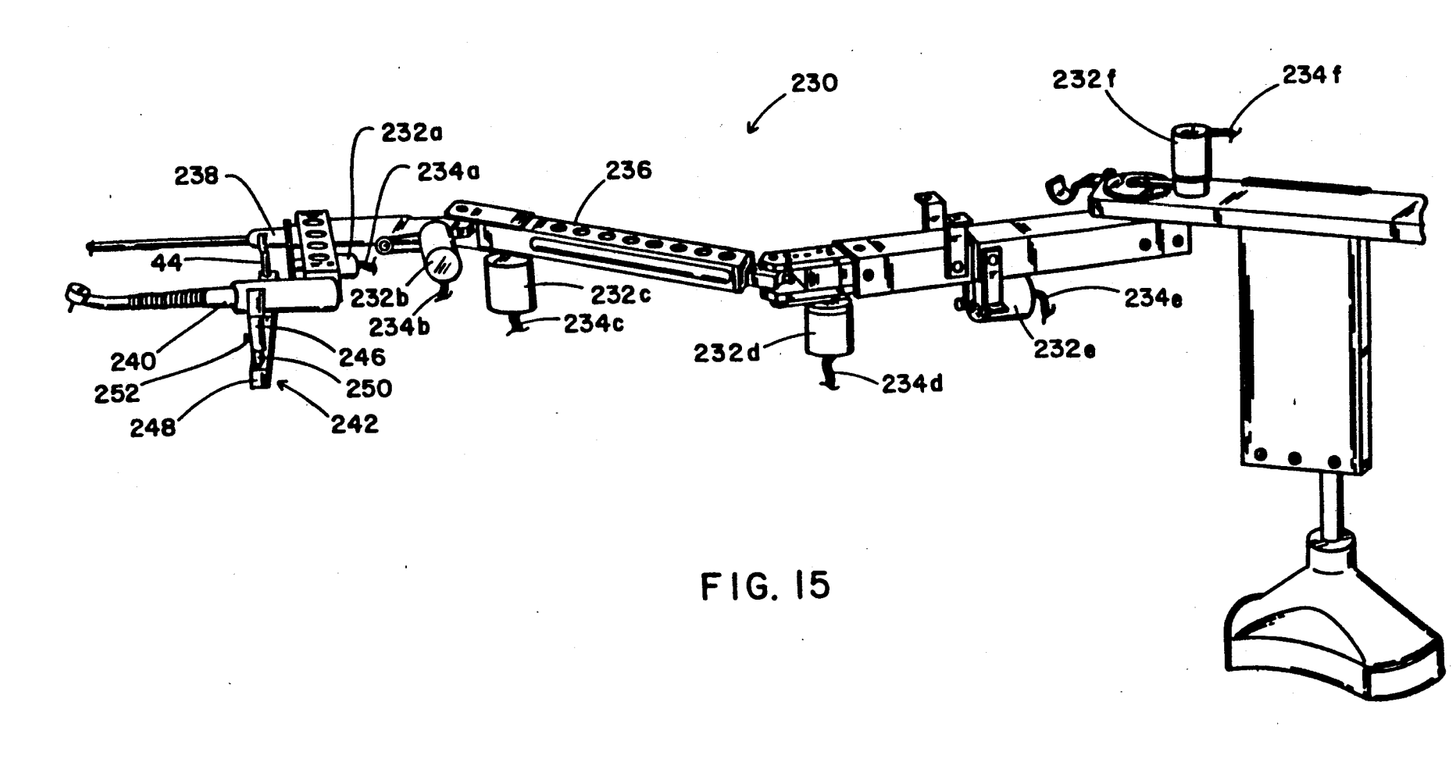
FIG. 15 is a perspective view of drill movement control assembly.

FIG. 15 illustrates a drill movement control assembly 230 similar in geometric design to the linkage 226 of FIG. 14. However, the encoders 22 of that linkage mechanism have been replaced in the movement control assembly of FIG. 15 with motors 232a-232f connected via respective energization leads 234a-234f to computer 24 (FIG. 1). In addition, in drill movement control assembly 230, the free end of a linkage 236 is connected to a pantograph arm 238 rather than to a drill member 240. Drill member 240 is rigidly but removably coupled to pantograph arm 238 via a U-shaped bridge 242 including a pair of legs 244 and 246 fastened to pantograph arm 238 and drill 240, respectively, and a transverse connector piece 248. Yet another leg member 250 is rigid with connector piece 248 and is telescopingly received inside leg 246. A spring loaded release latch 252 serves to removably clamp leg member 250 inside leg 246. Release latch 252 constitutes a safety mechanism enabling a dentist to remove drill 240 from a patient's mouth if the motion of the drill therein in response to operation of motors 232a-232f by computer 24 is not satisfactory to the dentist.

Upon the selection of a desired or optimum tooth preparation by a dentist and a subsequent signal for commencing tooth cutting, computer 24 generates a series of signals selecting energizing motors 232a-232f to move the operative end of drill 240 into engagement with those regions of the subject tooth which are to be removed to achieve the desired preparation. As described hereinabove, computer 24 controls the energization of drill 240 so that the drill is operative only in preselected zones in and about the regions of tooth to be removed.

Figure 16:
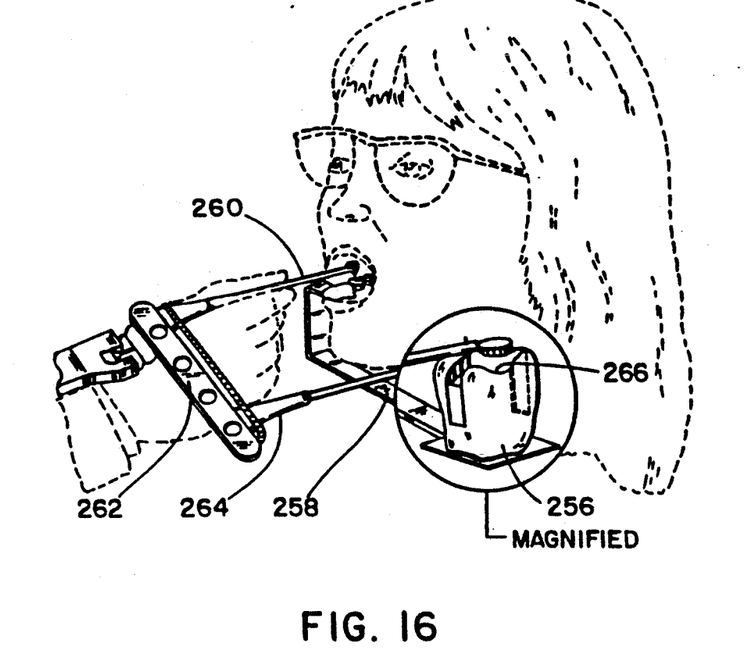
FIG. 16 is a partial perspective view, on an enlarged scale, of a drill movement restriction assembly, showing a tooth preparation preform on an even larger scale.

Limiting the motion of a dentist's drill 254 may be accomplished, in accordance with another feature of the invention shown in FIG. 16, by selecting a tooth preparation preform 256 from a kit of preforms. Preform 256 may be selected by computer 24, as described above, to confrom to a desired preparation or may be manually selected. Preform 256 is cemented to one end of a support bracket 258, the other end of which is attached to the patient's jaw wherein is rooted a tooth to be provided with the preparation of the selected preform. A pantograph assembly including a drill 260, a bridge member 262 and a pantograph arm 264 is then used to cut the tooth. A tip on the pantograph arm corresponding to the cutting tip of drill 260 is inserted into a cavity 266 in preform 256 (in the case of a filling or inlay). Engagement of the tip of pantograph arm 264 with the walls of cavity or recess 266 limits the concomitant motion of the drill, whereby the tooth is provided with a recess having the same geometric structure as recess 266.

Accordingly, pursuant to a particular feature of the invention, a kit is provided of dental preparation preforms in different sizes and shapes. Some preforms correspond to inlays such as that shown in FIG. 16. Other preforms correspond to onlays or crowns. The kit may also include prefabricated prosthetic devices, that is, preformed inlays and onlays for attachment to tooth surfaces upon preparation of those surfaces as described hereinabove.

Computer 24 has a data memory loaded with electrically encoded data corresponding to all of the preformed inlays and onlays in the kit. More specifically, the predefined tooth preparations selectable automatically by computer 24 or in response to instructions received via keyboard 40 or otherwise all correspond to respective prosthetic inserts of several predefined sizes.

Accordingly, computer 24 operates to select a desired tooth preparation and to control the formation of that preparation in the subject tooth. Upon the completion of the preparation, either the computer or the dentist selects the appropriately sized inlay or onlay. If necessary in a particular case, a selected preformed inlay or onlay can be machined prior to attachment to a tooth. Computer 24 may control the machining operations in a conventional numerically controlled operation or may serve to limit the range of cutting motions, as described hereinabove with reference to providing a tooth with the desired preparation.

Figure 17:
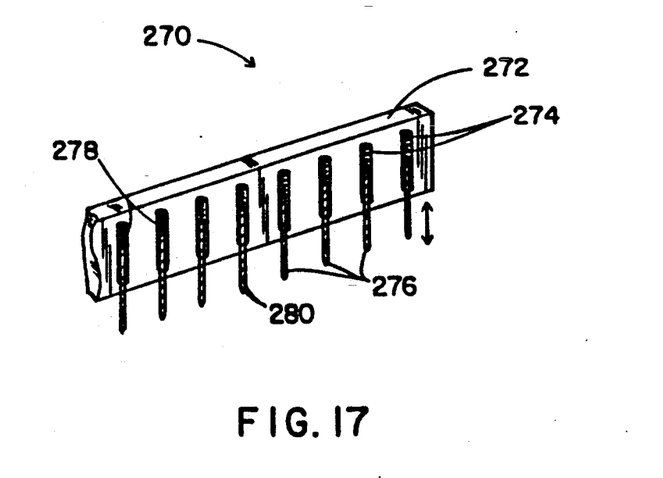
FIG. 17 is a partial schematic perspective view of a reference marker assembly.

FIG. 17 shows an assembly 270 for supplying surface data generating device 22 (FIG. 1) with optically detectable reference distances or displacements at the surface of the object (such as a tooth). Assembly 270 is attachable to the distal end of a dental probe such as instrument frame or holder 84 and comprises a holder member 272 made of transparent material and provided with a linear array of equispaced parallel bores 274 each slidably receiving a respective reference pin or stylus 276. Each stylus is pushed outwardly in a transverse direction relative to holder member 272 by a respective compression spring 278. In addition, each stylus 276 is provided with a series of longitudinally equispaced striations or reference marks 280.

The extensions of styli 276, i.e., the lengths to which the styli are pushed inside holder member 272, are measured by computer 24 through video signals obtained via a pair of optical pathways such as those illustrated in FIGS. 4 and 6. Alternatively, two optical light receiving elements such as prisms (not shown) may be placed on the same lateral side of the stylus array.

In using reference generator assembly 270 of FIG. 17, an operator such as a dentist presses styli 276 against a tooth surface. Under the pressure exerted by the operator, styli 276 are pushed respective distances into bores 274 against the action of springs 278. The displacement of each stylus 276 depends on and is a measure of a height of a respective surface element or zone of the tooth surface.

In most instances only a few (possibly as few as two) different positionings of stylus assembly 270 are required for computer 24 to map the entire surface of the tooth under observation.

Figures 18, 19:
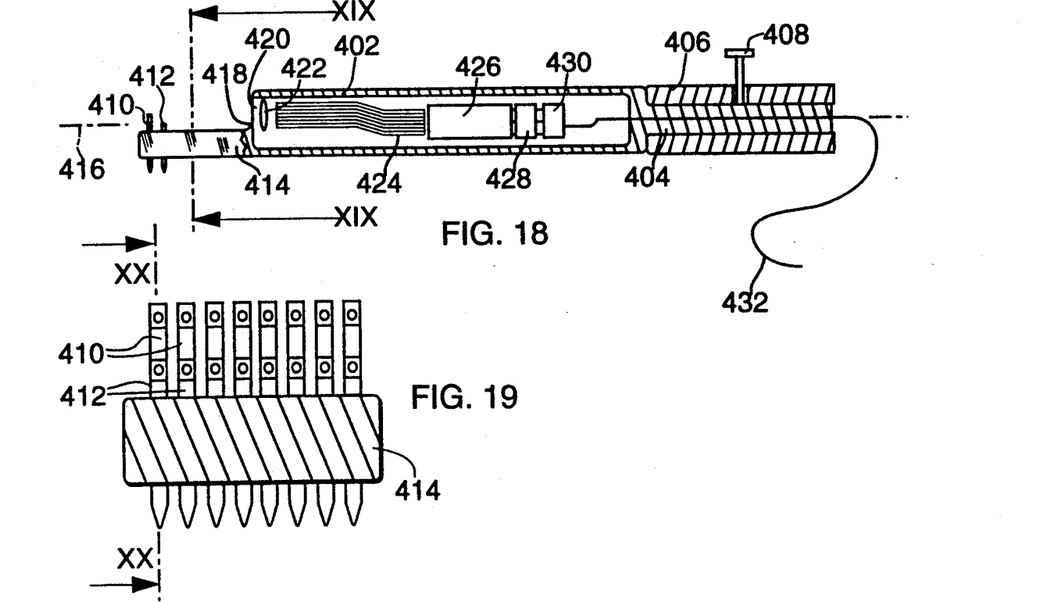
FIG. 18 is a side elevational view, partially in cross-section, of a hand held instrument usable in conjunction with a pantograph assembly illustrated in FIGS. 11–15, for gathering parallel contour data, in accordance with the present invention.
FIG. 19 is a cross-sectional view taken along line XIX—XIX in FIG. 18.

As illustrated in FIG. 18, a device for feeding to computer 24 (FIG. 1) contour data as to the surface of an object such as a tooth comprises a hand-held dental instrument or frame 402 provided at a proximal end with an extension 404 removably insertable into a sleeve 406 which forms a part of a pantograph assembly such as that illustrated in FIGS. 11 through 15. Instrument frame 402 is locked in a predetermined position and orientation to pantograph sleeve 406 by a set screw 408.

At a distal end, instrument frame 402 carries two sets of pins 410 and 412 slidably mounted to a nose portion 414 of instrument frame 401 in respective linear arrays extending at an angle, preferably a right angle, with respect to a longitudinal axis 416 of instrument frame 402.

Proximally of nose portion 414, instrument frame 402 has a shoulder 418 in turn formed with an opening or window 420 facing pins 410 and 412. A lens 422 is disposed at window 420 for focusing incoming light on an input end of a bundle of optical fibers 424 extending to a video camera in the form of a charge coupled device ("CCD") 426 inside instrument frame 402. CCD 426 is provided with conventional scanning circuitry 428 and output signal preprocessing circuitry 430. An output lead or multiple 432 extends from preprocessing circuitry 430 to computer 24 (FIG. 1).

Figure 20:
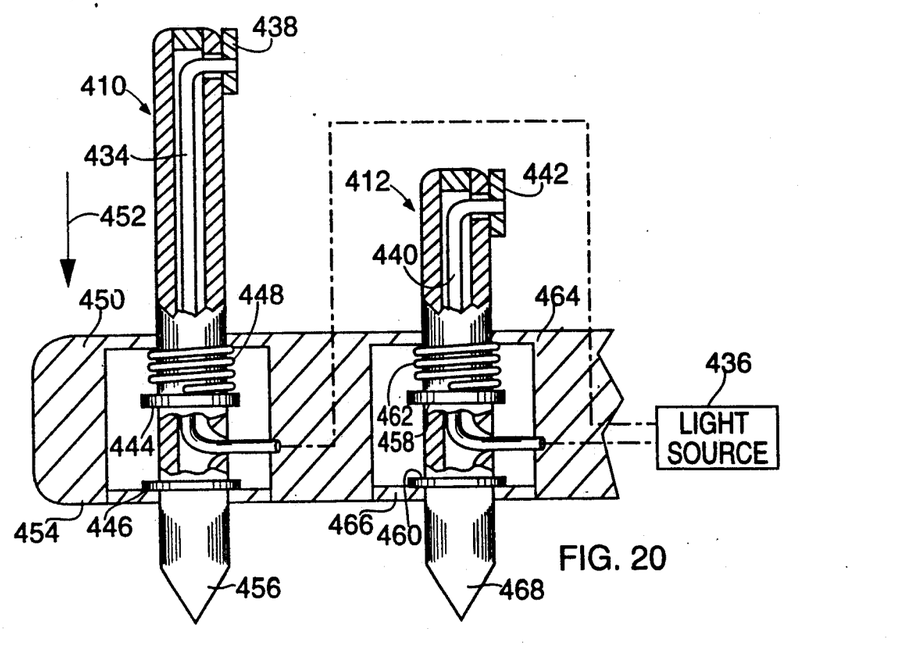
FIG. 20 is a partial cross-sectional view taken along line XX—XX in FIG. 19.

It is to be noted that other configurations of the operative components of the device of FIGS. 18-20 are possible and within the scope of the present invention. For example, CCD 426 and its associated circuitry 428 and 430 may be disposed at computer 24 or an intermediate location between the computer and instrument frame 402. In that configuration, optical fiber bundle 424 extends out from instrument frame 402 to the remote CCD. Alternatively, optical fiber bundle 424 may be omitted and CCD 426 positioned in juxtaposition to lens 422.

As depicted in FIGS. 19 and 20, each pin 410 is hollow and contains an end portion of a respective optical fiber 434 extending from a light source 436 inside instrument frame 402 to a mounting bracket 438 at an end of the respective pin 410. Each pin 412 is also hollow and contains an end portion of a respective optical fiber 440 extending from light source 436 to a mounting bracket 442 at an end of the respective pin 412. The distal ends of optical fibers 434 and 440, at mounting brackets 438 and 442, face lens 422, whereby the linear positions of pins 410 and 412 relative to nose portion 414 of instrument frame 402 may be instantaneously and continuously monitored by computer 24 through the video signals received from CCD 426.

As further depicted in FIG. 20, each pin 410 is provided with a pair of spaced perimetrically extending flanges 444 and 446. A helical spring 448 is compressed between a wall 450 of nose portion 414 and flange 444, thereby biasing the respective pin 410 in a direction indicated by an arrow 452. Flange 446 cooperates with another wall 454 of nose portion 414 to limit the distance that a pointed end 456 of the respective pin 410 projects from nose portion 414.

Each pin 412 is provided with a pair of spaced perimetrically extending flanges 458 and 460. A helical spring 462 is compressed between a wall 464 of nose portion 414 and flange 458, thereby biasing the respective pin 412 in a direction indicated by arrow 452. Flange 460 cooperates with another wall 466 of nose portion 414 to limit the distance that a pointed end 468 of the respective pin 412 projects from nose portion 414.

In using the contour data gathering device of FIGS. 18-20, a dental practitioner attaches the instrument frame 402 to pantograph-type component 50 (FIG. 1) via sleeve 406 and set screw 408, thereby fixing the instrument frame and pins 410 and 412 with respect to pantograph arm 56 which is monitored by optoelectrical transducers or video cameras 60 and 62. Pantograph component 50 enables computer 24 to track, from outside the mouth, the translatory motion of an arbitrarily selected reference point on instrument frame 402 inside the mouth of a patient. In addition, described hereinabove, pantograph assembly enables computer 24 to track the orientation of instrument frame 402 inside the patient's mouth. In this manner, computer 24 is continuously informed not only as to the position of the arbitrary reference point, but also the orientation of a coordinate system or reference frame, exemplarily with the reference point as origin.

It is to be noted that other methods for providing computer 24 with data as to the position and orientation of dental instrument 402 are possible. Instead of pantograph assembly, for instance, the encoders and articulated support arm assembly 310 of FIG. 14 may be utilized.

In addition to the data representing the location of an arbitrary reference point on instrument frame 402 inside a patient's mouth and the three-dimensional orientation of the instrument frame, computer 402 is supplied with a data stream from CCD 426 regarding the instantaneous positions of sliding pins 410 and 412. The dental practitioner presses pointed ends 456 and 468 of pins 410 and 412 against a dental surface and simultaneously draws instrument frame 402 along that surface. During this motion, pins 410 and 412 slide back and forth perpendicularly with respect to nose portion 414 in response to variations (pits and cavities, physical projections) in the surface of the tooth being scanned. These reciprocating motions tracing a plurality of parallel contours along the tooth surface are sensed by CCD 426 and quantized by computer 24 to form parallel contour data utilizable by conventional CAD/CAM programs previously loaded into computer 24.

The positional tracking of pins 410 and 412 by CCD 426 and computer 24 is facilitated by light output of optical fibers 434 and 440. Computer 24 measures the motions of pins 410 and 412 relative to the arbitrary reference point. Moreover, computer 24 is able to instantaneously correlate the incoming contour data stream(s) with the tooth surface being scanned, owing to the incoming rotational data as to the orientation of instrument frame 402 inside the patient's mouth.

Pins 410 and 412 are shown in FIG. 19 as being aligned with one another along the longitudinal axis 416 of instrument frame 402. However, contour data is collectible at an enhanced rate if the pins 410 of one row are staggered with respect to the pins 412 of the other row. Such a two-dimensional array of pins 410 and 412 enables a greater pin density, thereby increasing the amount of incoming contour data.

Instrument frame 402 may be provided with a button (not shown) which, when pressed by the dentist, provides computer 24 with a signal that contour data input is commencing.

Figure 21:
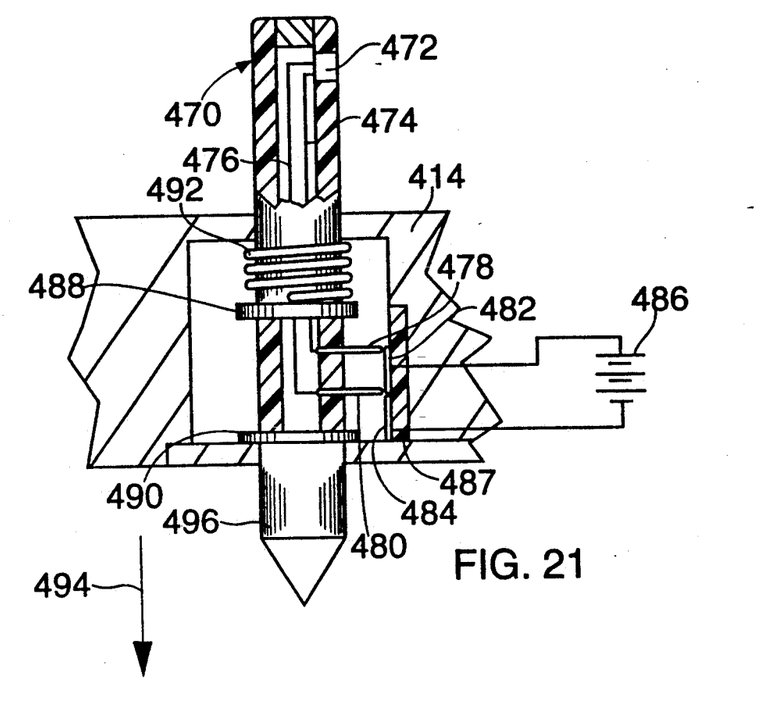
FIG. 21 is a partial cross-sectional view similar to that shown in FIG. 20, showing a modified parallel contour data gathering device in accordance with the present invention.

FIG. 21 depicts another pin or stylus 470 slidably mounted to nose portion 414 of instrument frame 402 in substitution for pins 410 and/or 412. In pin 470, a light-emitting diode 472 forms the light source for facilitating detection by CCD 426 (FIG. 18) and monitoring by computer 24. Diode 472 is connected by a pair of leads 474 and 476 to two brush-type terminals 478 and 480 which are in sliding contact with respective plates 482 and 484. Plates 482 and 484 are connected to opposite terminals of a direct-current voltage source 486 and are insulated from nose portion 414 by a buffer element 487.

As further depicted in FIG. 21, each pin 470 is provided with a pair of spaced perimetrically extending flanges 488 and 490. A helical spring 492 is compressed between wall 450 or 464 (see FIG. 20) of nose portion 414 and flange 488, thereby biasing the respective pin 470 in a direction indicated by an arrow 494. Flange 490 cooperates with wall 454 or 466 of nose portion 414 to limit the distance that a pointed end 496 of the respective pin 470 projects from nose portion 414.

Figure 22:
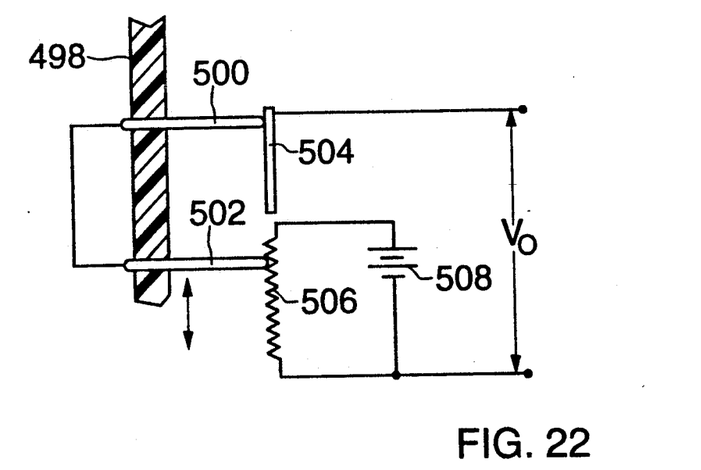
FIG. 22 is a diagram showing a circuit of another parallel contour data gathering device in accordance with the present invention.

FIG. 22 illustrates a portion of a pin or stylus 498 slidably mounted to a nose portion (e.g. 414 in FIG. 18) of a dental instrument for providing computer 24 (FIG. 1) with digitized data representing a surface contour on a tooth. As described hereinabove with reference to FIGS. 18-20, pin or stylus 498 is one of a plurality of identical stylii all slidably mounted to the nose portion of the instrument frame in a linear or two-dimensional array for providing contour data along a plurality of parallel planes. As further described above with reference to FIGS. 18-20, the dental instrument carrying pins 498 is removably attachable to pantograph-type component 50 (FIG. 1), whereby computer 24 is also provided with digitized data representing the location and orientation of a distal end of the dental instrument inside a patient,s mouth during use of the dental instrument.

A pair of brush type contacts 500 and 502 are embedded in stylus 498 and operatively engage in a sliding contact a plate 504 and a resistive element 506, respectively. A direct-current voltage source 508 is connected across resistive element 506, while an output voltage $v_0$ is taken across a portion of resistive element 506 depending on the distance that stylus 498 is shifted with respect to the instrument. Output voltage $v_0$ thus represents the displacement of stylus 498 and is fed to an analog-to-digital converter (not shown) prior to being fed to computer 24.

Figure 23:
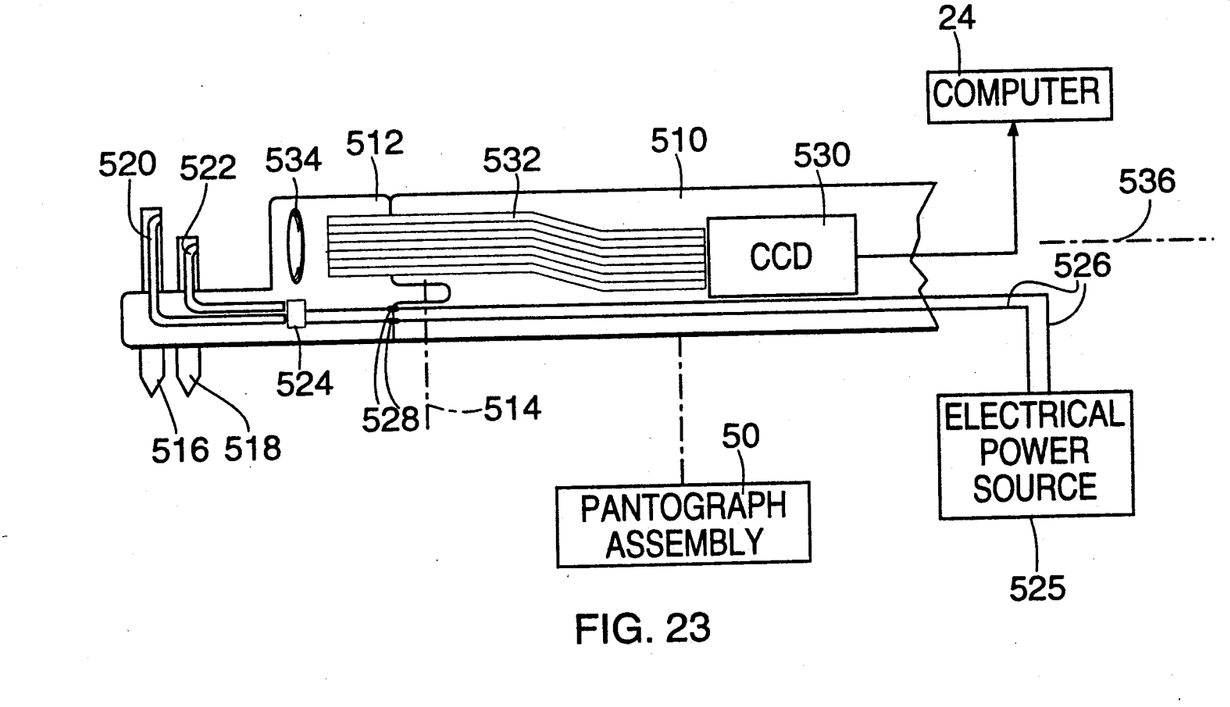
FIG. 23 is a schematic side elevational view of yet another parallel contour data gathering device in accordance with the present invention.

As shown in FIG. 23, a parallel contour data gathering device includes an instrument frame or body 510. A nose portion 512 is pivotably attached to a distal end of frame 510 for rotation about an axis 514. Nose portion 512 carries two linear arrays of pins or stylii 516 and 518 slidably mounted to the nose portion as described hereinabove with reference to FIGS. 18-20. Pins 516 and 518 are partially longitudinally traversed by respective optical fibers 520 and 522 extending from a diode 524 in nose portion 512. Diode 524 in turn is energized by a source of electrical power via a pair of leads 526. Leads 526 include a pair of sliding or brush type contacts 528 for enabling the conduction of electrical energy to diode 524 over the rotating link between frame 510 and nose portion 512.

A reciprocating type motion of pins 516 and 518 which occurs as a dentist moves nose portion 512 along a tooth surface is monitored by computer 24 via digitized video signals arriving from a charge-coupled device ("CCD") and its associated preprocessing circuitry 530. CCD 530 receives optical energy via a bundle of optical fibers 532 extending from a lens 534 in nose portion 512.

The pivoting attachment of nose portion 512 to frame 510 facilitates the collection of parallel contour data by enabling a dentist to orient nose portion at an angle (e.g. a right angle) with respect to a longitudinal axis 536 of instrument frame 510. The angular orientation of nose portion 512 particularly facilitates the collection of parallel contour data along a plurality of parallel planes oriented at the aforementioned angle with respect to axis 536. Computer 24 is able to take the orientation of nose portion 512 into account by monitoring, via pantograph assembly 50, the direction of motion of the distal end of instrument frame 510 during a data gathering motion thereof.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are preferred by way of example to facilitate comprehension of the invention and should not be construed to limit the scope thereof.

What is claimed is:

1. A device for providing a computer with electrically encoded data specifying curvilinear contours of an object, said device comprising:
   a manipulable frame member;
   reference position establishing means for transmitting to said computer an electrical signal encoding a location of a reference point on said frame member;
   a plurality of stylus elements each slidably mounted to said frame member for motion along respective axes extending at least partially parallel to one another; and
   a stylus displacement measuring means operatively connected to said stylus elements for transmitting to said computer electrical signals encoding displacements of said stylus elements along the respective axes.

2. The device defined in claim 1 wherein said reference position establishing means includes a pantograph extension rigid with said frame member and scanning means for optically scanning the location of a point on said pantograph extension and transmitting a resulting video signal to said computer.

3. The device defined in claim 2, further comprising reference means for enabling said computer to determine, via video signals from said scanning means, the location of said point on said pantograph extension relative to said object.

4. The device defined in claim 3 wherein exactly one of said reference means and said scanning means is fixed relative to said object.

5. The device defined in claim 3 wherein said reference means includes a grid attached to the object.

6. The device defined in claim 2 wherein said scanning means includes at least two cameras.

7. The device defined in claim 2 wherein said scanning means includes a solid state optical sensor and means for attaching said sensor to the object.

8. The device defined in claim 1 wherein said stylus displacement measuring means includes scanning means for optically scanning points on said stylus elements.

9. The device defined in claim 8 wherein said stylus elements are provided with light emitting elements.

10. The device defined in claim 1 wherein said styl displacement measuring means includes a plurality of voltage dividers.

11. The device defined in claim 1, further comprising means for spring biasing said stylus elements into extended positions relative to said frame member.

12. The device defined in claim 1 wherein said stylus elements are disposed in a linear array.

13. The device defined in claim 1 wherein said stylus elements are disposed in a two-dimensional array.

14. The device defined in claim 1, further comprising means for transmitting a signal to said computer that data input from said stylus displacement measuring means is taking place.

15. A method for providing a computer with digitized data encoding surface features of a three-dimensional object, comprising the steps of:
   providing a manipulable frame member having a plurality of stylus elements each slidably mounted to said frame member for motion along respective axes extending at least partially parallel to one another;
   tracing at least one surface contour on the threedimensional object with said manipulable frame member so that said stylus elements are in contact with said object;

transmitting to said computer an electrical signal encoding a location of a reference point on said frame member during said step of tracing; and transmitting to said computer electrical signals encoding displacements of said stylus elements along the respective axes during said step of tracing.

16. The method defined in claim 15 wherein said manipulable frame member is provided with a pantograph extension rigid therewith, said step of transmitting to said computer an electrical signal encoding a location of a reference point including the step of optically scanning the location of a point on said pantograph extension and transmitting a resulting video signal to said computer.

17. The method defined in claim 15 wherein said step of transmitting to said computer electrical signals encoding displacements of said stylus elements includes the step of optically scanning points on said stylus elements.

18. The method defined in claim 15 wherein said step of transmitting to said computer electrical signals encoding displacements of said stylus elements includes the step of generating electrical signals using a plurality of voltage dividers.

19. The method defined in claim 15, further comprising the step of signaling said computer that data input from said stylus displacement measuring means is taking place.

* * * * *